United States Patent
Bonner et al.

(10) Patent No.: US 10,980,827 B2
(45) Date of Patent: Apr. 20, 2021

(54) COMPOSITION FOR DUST PARTICLE REDUCTION

(71) Applicant: Johnson & Johnson Consumer Inc., Skillman, NJ (US)

(72) Inventors: Patricia Bonner, Branchburg, NJ (US); Amanda Hernandez, Mercerville, NJ (US); Prithwiraj Maitra, Hillsborough, NJ (US); Jiger J. Patel, Somerset, NJ (US); Meenakshi Lalit Patel, Voorhees, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 71 days.

(21) Appl. No.: 15/279,626

(22) Filed: Sep. 29, 2016

(65) Prior Publication Data

US 2017/0087176 A1 Mar. 30, 2017

Related U.S. Application Data

(60) Provisional application No. 62/234,209, filed on Sep. 29, 2015.

(51) Int. Cl.
*A61K 31/718* (2006.01)
*A61Q 19/00* (2006.01)
*A61K 8/73* (2006.01)
*A61K 8/19* (2006.01)
*A61K 9/00* (2006.01)
*A61K 9/14* (2006.01)
*A61K 9/16* (2006.01)
*A61K 31/717* (2006.01)

(52) U.S. Cl.
CPC .............. *A61K 31/718* (2013.01); *A61K 8/19* (2013.01); *A61K 8/73* (2013.01); *A61K 8/731* (2013.01); *A61K 8/732* (2013.01); *A61K 9/0014* (2013.01); *A61K 9/146* (2013.01); *A61K 9/1652* (2013.01); *A61K 31/717* (2013.01); *A61Q 19/005* (2013.01)

(58) Field of Classification Search
CPC .... A61K 31/715; A61K 47/38; A61K 31/718; A61K 31/717; A61K 8/022; A61K 8/19; A61K 8/73; A61K 8/731; A61K 8/732; A61K 9/0014; A61K 9/146; A61K 9/1652; A61P 17/00; A61Q 19/005

USPC .............................................. 514/54, 57, 60
See application file for complete search history.

(56) References Cited

U.S. PATENT DOCUMENTS

| | | | | |
|---|---|---|---|---|
| 4,120,952 | A * | 10/1978 | Cardon | A61K 31/715 514/60 |
| 4,269,859 | A * | 5/1981 | Morse | A61K 9/2054 264/117 |
| 4,701,445 | A * | 10/1987 | Shull | A61K 31/715 514/54 |
| 6,471,944 | B1 * | 10/2002 | Uchiyama | A61K 9/12 424/45 |
| 6,656,487 | B2 | 12/2003 | Afriat et al. | |
| 7,594,619 | B2 | 9/2009 | Ghere, Jr. et al. | |
| 9,364,416 | B2 | 6/2016 | Bonner et al. | |
| 9,370,478 | B2 | 6/2016 | Bonner et al. | |
| 2003/0143293 | A1 * | 7/2003 | Shushunov | A61K 33/14 424/773 |
| 2006/0029625 | A1 | 2/2006 | Niebauer | |
| 2014/0134217 | A1 * | 5/2014 | Bonner | A61K 8/11 424/401 |

FOREIGN PATENT DOCUMENTS

| | | | |
|---|---|---|---|
| EP | 2332519 A | 6/2011 | |
| JP | 03052818 A * | 3/1991 | |
| WO | WO-0125315 A1 * | 4/2001 | ............... C08J 3/12 |
| WO | WO-2013122127 A1 * | 8/2013 | ............... C08L 5/00 |
| WO | WO 2014/074578 A | 5/2014 | |
| WO | WO 2014/074583 A | 5/2014 | |

OTHER PUBLICATIONS

W200 White Cotton Flock, IFC product data sheet, date issued Dec. 12, 2012, distributed by Freeman Manufacturing & Supply Co., 1 page. (Year: 2012).*
Alcázar-Alay et al., Food Science and Technology Campinas, 2015, 35(2), p. 215-236. (Year: 2015).*
International search report dated Mar. 3, 2017 for PCT/US2016/054328.

* cited by examiner

*Primary Examiner* — Jonathan S Lau
(74) *Attorney, Agent, or Firm* — Laura A. Donnelly (57) ABSTRACT

Combination powdered material, including a first powder composition and a second powder composition, the first powder composition including cellulose particulate material and the second powder composition including starch particles, alone or in combination with talc particles.

4 Claims, 5 Drawing Sheets

Figure 2 - 100% talc

Figure 3 - 100% cornstarch

Figure 4 – 100% cellulose particles

Figure 5 – 50%/50% cellulose particle and cornstarch

COMPOSITION FOR DUST PARTICLE REDUCTION

This application claims the benefit of U.S. provisional application 62/234,209 filed on Sep. 29, 2015, the complete disclosure of which is hereby incorporated by reference for all purposes.

FIELD OF THE INVENTION

The present invention relates to materials and compositions suitable for reducing the release of particulates in a powdered material. Specifically, the materials useful herein are effective in reducing the release of particulates in a powder to be applied to the skin, and especially the skin of babies.

BACKGROUND

For years, individuals have been applying powder-based materials and compositions to skin to provide a beneficial effect. In many instances, these compositions are applied to the skin of babies and young children to help reduce skin irritation and rash. Such compositions are commonly referred to as "baby powder", and may include components such as cornstarch or talc.

However, being a particulate composition, it is difficult to accurately and precisely apply such baby powder to the exact target location of the skin of the user, as there is a tendency of small components to be "dusted", that is, smaller particles of the composition are released into the air in the vicinity of the skin to which the composition is to be applied. This release of powder, or dusting, reduces the amount of material actually applied to the target site.

There is currently a need to provide components and materials to known powdered compositions to reduce the "dusting" effect, in order to reduce dusting and to more accurately apply the powder composition to the target site.

SUMMARY

In one aspect of the invention, there is a combination particulate composition that is effective in providing beneficial effect to the skin of a user, while controlling the airborne dusting when applied or manufactured, and also increasing the precision and/or accuracy of application when dispensed onto the skin of a user. The combination particular composition may include a first powder component including a plurality of particles including starch or a polysaccharide bearing at least one hydroxyl moiety and a second powder component including a plurality of particles including linear hydrophobic cellulose particles.

The invention may further include a method of reducing dusting of a particulate composition including combining a first powder component including a plurality of particles including starch or a polysaccharide bearing at least one hydroxyl moiety with a second powder component including a plurality of particles including linear hydrophobic cellulose particles, thereby forming a combination particulate composition with a lesser dusting profile than a composition without the second powder component.

Kits and packaged products including the combination particulate composition may be included and provided to a user for application and use by the user.

BRIEF DESCRIPTION OF FIGURES

FIGS. 2-7 are photographs of the results of tests done in Example 1 of the present invention:

DETAILED DESCRIPTION

The present invention relates to components and materials for use in powdered compositions, as well as the resulting combination material including powdered compositions with added components or materials. The resulting combination particulate material has a reduced tendency to release particles airborne during use ("dusting", described below), and also provides a more controlled and localized accuracy when applying to a target site.

As used herein, the term "particle" or "particulate" means a small localized object to which can be ascribed physical properties such as volume or mass. As used herein, "powder" is used to refer to a composition including a plurality of "particles", as defined herein. A particle may be spherical but need not be spherical, it may have a length and width (or diameter), thereby providing an aspect ratio greater or less than 1. In some aspects, the particle may have an amorphous shape.

The compositions described herein are useful for application to a body, and specifically to the skin of a body, such as human skin. The human skin to which compositions described herein is useful includes, for example, adult skin, baby skin, or skin of a young child, such as a toddler. Compositions described herein may be used on skin that has a higher sensitivity to irritation, or skin that has a lower sensitivity to irritation.

Certain powders are known to be beneficial when applied to skin, such as to provide a reduction in irritation or to prevent rash or itching. Particularly in the case of application to babies, it is known to use "baby powder" on the skin of a baby. However, the term "baby powder" does not limit its application to babies alone, and such baby powder products may be applied to the skin of older children or adults. In some territories, baby powder may include or consist essentially of starch or polysaccharides bearing hydroxyl moieties (such as cornstarch), while in other territories, baby powder may include or consist essentially of talc, while in still other territories, baby powder may include combinations of cornstarch and talc. Baby powder may include other ingredients (referred to as "Additional Baby Powder Components"), such as fragrances or perfumes, including oils or extracts such as aloe, lavender, and chamomile, or may include cooling agents such as menthyl lactate and isopulegol. Other Additional Baby Powder Components include, for example, opacifying agents, including calcium salts such as tricalcium phosphate; bulking agents such as magnesium stearate; antioxidants, such as sodium ascorbyl phosphate; preservatives, such as chloroxylenol; parabens, such as propylparaben or methylparaben, vitamins such as Vitamin E; sun agents such as zinc oxide; humectants, such as betaines or glycerin; pH adjusters, including acids and citrates; skin conditioners, such as milk protein, copper gluconate, magnesium aspartate, zinc gluconate, panthenol, tocopheryl acetate, and propylene glycol; sodium bicarbonate, bisabolol, tocopherol, silica; and other materials that may be added to commercial powders. The term "consisting essentially of" as used herein with reference to a baby powder composition does not preclude the use of these Additional Baby Powder Components. By way of example, a fragrance or mixture of fragrances may be included in the baby powder composition in an amount of from about 0.01% to about 0.5% by weight of the baby powder composition. Similarly, by way of example, opacifying agents such as calcium salts may be present in an amount of from about 0.25% to about 0.75% by weight of the baby powder composition.

Baby powder includes a powdered composition that may be applied to the skin of a human, and may include starch or polysaccharides bearing hydroxyl moiety, talc, and/or clay-derived substances (such as kaolin). The term "starch" includes a polysaccharide consisting of a large number of glucose units joined by glycosidic bonds, including starch derived from sources such as corn and tapioca, and the term "cornstarch" refers to starch specifically obtained from corn. Cornstarch may include trace amounts of minerals such as iron, sulfur dioxide, ash, and oxidizing substances, which are inherent in cornstarch. Cornstarch powder useful in the present invention may have a moisture percentage of about 11.5% or less, where about 100% of the particles pass through a 60 mesh (U.S.S.) screen, greater than about 99% of the particles pass through a 100 mesh screen, and greater than about 98% of particles pass through a 200 mesh screen. Suitable cornstarch may be supplied by Ingredion, under the trade name Corn Products™, powdered dusting corn starch 034500. For this application, when the terms "cornstarch" or "cornstarch powder" are used to describe a composition, that composition consists essentially of cornstarch (but it may include Additional Baby Powder Components identified above, such as fragrance, humectants, calcium salts, or preservatives).

The term "talc" or "talcum powder" means a natural hydrous magnesium silicate mineral, which may be beneficiated, milled, and processed to a fine white powder. The term "talc" or "talcum powder" may include minerals such as dolomite and/or chlorite, which are inherently found in high purity talc. The amount of additional (non-talc) minerals is about 2% or less by weight of the talcum powder. Suitable talc includes about 99.5% or greater of the particles passing through a 200 mesh screen (U.S.S.), with a median diameter of about 10.5 microns particle size distribution. Suitable talc may be supplied by Luzenac, under the trade name Grade 25 USP talc. For this application, when the terms "talc" or "talc powder" is used to describe a composition, that composition consists essentially of talc (but it may include Additional Baby Powder Components identified above, such as fragrance, opacifying agents, or preservatives).

The present invention provides various components to be added to or combined to form baby powder compositions, as well as the resulting combination of baby powder compositions and such added materials, as well as methods of making and methods of using such resulting combination of baby powder compositions and added materials.

In one particular embodiment, the resulting combination product includes baby powder mixed with a desirable amount of a particulate cellulosic material, and in some embodiments, that cellulosic material may be powdered material obtained from cotton. The baby powder may be a powdered cornstarch composition, or it may be a powdered cornstarch/talc combination material. Thus, the resulting combination product described herein may include particulate cellulosic material with powdered cornstarch, or it may include particulate cellulosic material with powdered cornstarch and talc, or it may include particulate cellulosic material with powdered cornstarch and clay-derived materials, such as kaolin. Additional Baby Powder Components identified above may also be included.

It has been discovered by the present inventors that the addition of cellulosic materials in a particulate or powdered form can provide significant benefit to baby powder, specifically baby powder including cornstarch or consisting essentially of cornstarch. The combination powder can be applied more accurately, with less risk of dusting, and still provide a benefit to the skin, such as reduction in irritation, reduced likelihood of rash or irradiation, and the like. It is particularly preferred that the cellulosic materials consist of cotton or consist essentially of cotton, as will be described below, to maintain a low risk of irritation and rash.

The cellulosic materials are particulate, and may be spherical, amorphous, or linear particles, or combinations thereof. As used herein, the term "linear particle" means a particle having one dimension ("length") that is greater than another dimension (e.g., "diameter" or "width"). Linear particles may be measured and defined by size by subjecting such particles to analysis with respect to a series of sieves having different mesh sizes. Generally, a sample of linear particles may have a distribution of particle sizes throughout the sample. Thus, linear particle sizes as expressed herein are expressed as an average particle size and reflect the average length of the particles contained within the sample. A linear particle need not be perfectly straight or have a consistent width and/or length throughout, it may have some irregular sides and still be considered substantially linear.

Preferably, the average size of linear particles useful in the compositions and methods of this invention is less than about 1000 μm in length, or less than about 700 μm in length, or less than about 500 μm in length, or more preferably, it ranges from about 2 to about 1000 μm, or from about 50 to about 700 μm, or from about 100 to about 600 μm. The width or diameter of linear particles useful in the compositions and methods of this invention is about 1 to about 100 μm, or from about 2 to about 50 μm in width or diameter, or from about 2 to about 40 μm in width or diameter.

As used herein, the term "particle aspect ratio" means the ratio of the length of a particle to its width or diameter. Preferably, the particle aspect ratio of linear particles useful in the compositions and methods of this invention is from about 2 to about 20. More preferably, the particle aspect ratio is from about 2 to about 15 and most preferably, from about 2 to about 10. The particulate compositions used herein may include linear particles and spherical particles in combination, if desired.

As used herein, the term "cellulose" refers to a polysaccharide material consisting of long unbranched chains of linked glucose units.

Cellulose materials useful in the compositions and methods of this invention may be derived from cotton, corn, wood pulp and bamboo pulp, silk, cork and the like. Preferably, the cellulose materials useful in the compositions of this invention are derived from cotton. The cellulosic particles may be from fibers recovered from post-industrial scrap or may be derived from raw cotton. Scrap is derived from waste or other pre-consumer cotton products from, for example, the apparel, carpet, furniture and household goods industries. Synthetic or regenerated cotton or cellulose materials may also be used as sources for the cellulose particles useful in the compositions and methods of this invention, including rayon, viscose, cellophane, and other cellulosic materials with a uniform and reproducible molecular size and distribution.

The cellulose materials useful in the compositions and methods of this invention may be derived directly from the source plant (referred to herein as, "Raw" particles) or may be generated from cloth or nonwoven materials previously formed from plant or cellulose fibers (referred to herein as "regenerated" particles). For example, cotton cloth may be processed so as to break the cloth into small particles and/or fiber lengths by cutting the length of the cotton fibers from inches to microns. This cut fiber is available in several grades, white, dark, and unbleached, with average fiber lengths described above. The cut fibers may be substantially uniform in length and/or width, or may be random.

Typical mechanical milling processes such as those useful in cutting down the size of the cellulose materials useful in the compositions and methods of this invention, for example, are described in U.S. Pat. Nos. 7,594,619 and 6,656,487, which are hereby incorporated herein by reference.

Generally, the cellulose particles useful in the compositions of this invention may be processed according to the any known methods. One such method comprises mixing a cellulosic material derived from scrap, as defined above, with at least one of grinding aids selected from the group including water, fatty acids, synthetic polymers and organic solvents, and, after mixing, mechanically grinding the mixture.

Another method of obtaining cellulose particles is freezing a cellulosic material derived from post-industrial scrap at a low temperature, and then mechanically grinding said frozen material. Cellulose particles useful herein may be hydrophobic or may be hydrophilic.

The cellulose particles useful in the compositions and methods of this invention may be further treated with hydrophobic agent(s) to yield more hydrophobic cellulose particles. For example, a hydrophobic coating agent may be used to treat the cellulose particles. The hydrophobic coating agent may be any such agent known to one of skill in the art. Hydrophobic coating agents react chemically with the cellulose particles to provide a durable covalent bond thereto and have hydrophobic chemical backbones or substituents that can provide a hydrophobic outer layer around each individual cellulose particle. The coating agent may react, for example, with hydroxyl groups, available oxygen atoms present on the surface of the cellulose particle being coated.

Hydrophobic agents may include, but not limited to, low water soluble organic compounds such as metal soap, e.g., a metal myristate, metal stearate, a metal palmitate, a metal laurate or other fatty acid derivatives known to one of skill in the art. Other hydrophobic agents may include an organic wax, such as a synthetic wax like polyethylene or a natural wax like carnauba wax. Hydrophobic agents useful in coating the cellulose particles useful in the compositions and methods of this invention may also be long chain fatty acids or esters such as stearic acid, oleic acid, castor oil, isododecane, silicone, and their derivatives, non-water soluble polymers, e.g. high molecular weight methylcellulose and ethylcellulose, and high molecular water insoluble fluoropolymers etc., polymerized siloxanes or polysiloxanes with the chemical formula [R2SiO]n, where R is an organic group such as methyl, ethyl, or phenyl, such as dimethicone, dimethicone copolyol, dimethicone ester; methicone and their derivatives. Examples of hydrophobic linear cotton particles useful in the present invention include, but are not limited to, Cotton Fiber Flock CD60 available from Goonvean Fiber and W200 and W325 White Cotton Flock available from International Fiber Corporation.

The combination material prepared from the present invention includes a first powdered component consisting essentially of cellulose powder, and a second powdered component including baby powder. The baby powder of the second powdered component may include or consist essentially of starch (such as cornstarch), clay-based materials, and/or talc. It is preferred that the average size of the particles of the first powdered component and the second powdered component be substantially similar, that is, when mixed together, the first powdered component and the second powdered component are not easily separable from each other due to their relative sizing.

The combination material may include any desired amounts of the first powdered component and the second powdered component. For example, there may be from about 5% to about 80% of the first powdered material by weight of the combination material, or about 10% to about 50% of the first powdered material by weight of the combination material, or about 10% to about 40% of the first powdered material by weight of the combination material, or about 15% to about 20% of the first powdered material by weight of the combination material. The remaining material(s) forming the combination material may include the second powdered component, which may include or consist essentially of starch (such as cornstarch), clay-based materials, talc, or combinations thereof (such as talc and starch in combination).

Thus, in one embodiment, a combination material includes a first powdered component including or consisting essentially of cellulose particles in an amount of about 5-20% by weight of the combination material, and a second powdered component including or consisting essentially of starch particles in an amount of about 80-95% by weight of the combination material. An alternative combination material includes a first powdered component including or consisting essentially of cellulose particles in an amount of 75% by weight, and a second powdered component including or consisting essentially of starch particles in an amount of about 25% by weight. An alternative combination material includes a first powdered component including or consisting essentially of cellulose particles in an amount of about 5-50% by weight of the combination material, and a second powdered component including or consisting essentially of starch particles in an amount of about 25-50% by weight of the combination material, and an optional third powdered component including or consisting essentially of talc particles in an amount of about 25-45% by weight of the combination material. As noted above, the relative percentages may vary, with the first powdered component being present in an amount as described above, and the second powdered component (or second and third powdered components) forming the remaining part of the combination material.

The combination of the first powdered component and second powdered component (and optional third powdered component) may equal 100% of the final composition, or the combination may equal less than 100% of the total composition, if Additional Baby Powder Components such as fragrances, dyes, preservatives, vitamins, dyes, humectants, emollients or other additives are included in the final combination particulate composition. For example, the combination particulate composition may include a first powdered component and a second powdered component, and optionally a third powdered component, in an amount totaling about 95% to about 99.99% by weight of the combination particulate composition, with the remaining 0.01-5% of the combination particulate composition including Additional Baby Powder Components described above, such as added vitamins, fragrances, humectants, or other additives, alone or in combination with other Additional Baby Powder Components. In some instances, the amount of Additional Baby Powder Components may be up to 10% by weight of the final composition, or may be from about 0.01-5% by weight of the final composition, or may be from about 0.1-2% by weight of the final composition.

It is desired that there be as little water or aqueous material in the resulting combination material as practical, with the understanding that certain powdered materials may inherently absorb moisture. Desirably, the resulting combination material includes less than 1% by volume aqueous material or less than 0.1% by volume aqueous material, such as water.

The Applicant has discovered that the incorporation of a cellulose powder material into a powdered cornstarch composition provides benefits, including, for example, reduction in the amount of airborne dust particles and more targeted delivery of the combination composition. By way of example, it is noted that incorporating about 50% cellulose powder into a powdered cornstarch composition reduces the amount of airborne dust particles of a cornstarch composition alone by about 140%. In addition, the Applicant has discovered a reduction in airborne dust particles when there is a "one for one" replacement of both cornstarch and talc with cellulose powder. When compared to a cornstarch composition alone, the inclusion of cellulose powder reduces the amount of airborne dust particles by about 340%. When compared to a talc composition alone, inclusion of cellulose powder reduces the amount of airborne dust particles by about 1650%. Other benefits and levels are set forth in the Examples below.

Surprisingly, however, the Applicant has discovered that the inclusion of cellulose particles into a composition consisting essentially of talc powder does not necessarily have an effect of reducing the amount of dust borne particles when cellulose is added at certain amounts. This will be discussed in more detail below in the Examples, but this demonstrates that inclusion of cellulose particles into any powdered composition does not inherently cause a reduction in the amount of airborne dust particles into the air during use. Further, it can be seen that addition of certain levels of cellulose into compositions has a different affect based upon the amount of cellulose and the type of other components in the composition. For example, while cellulose in a cornstarch composition provides benefit at various levels tested, it actually provided increased benefit when added in lower amounts. When added to talc compositions, the benefit increased as cellulose was increased, but once the amount of cellulose reached a certain level (50%), the benefit was not seen and dusting increased. Thus, the present inventors have discovered a surprising and unexpected benefit when cellulose is added to compositions including cornstarch, where the benefit is not inherently seen in every powdered composition.

The combination materials of the present invention should include at least a first powdered composition including cellulose particles and a second powdered composition consisting essentially of starch or any polysaccharides bearing hydroxyl moieties (such as cornstarch), and may optionally include a third powdered composition consisting essentially of talc or clay-based components.

The combination powdered material may be prepared by any desired methods, including, for example, simple mixing by combining materials in a container and stirring or shaking to combine the materials. Other equipment for mixing materials may be used, including, for example, using a rotary batch mixer, a vee-cone blender, a fluidized bed mixer, a ribbon, paddle and plow blender, continuous blenders, and the like. If wet ingredients are included, they may be incorporated by spraying into a mixer before, during or after mixing of the dry (powdered) components. After blending, there is desired a substantially homogenous distribution of a first powdered component and second powdered component, as described above.

The combination material described herein may be used by applying the combination material directly or indirectly to the skin of a human, including, for example, the skin of an adult human, a baby human, or a child human. The combination material may be applied to any skin region desired, and may be left in place after application or may be rubbed or otherwise massaged onto the skin after application. In some embodiments, the combination material may be applied to an applicator, which may be a fabric or cotton applicator or wipe, or in some instances may be the hand of a user, and then applied to the target skin region. The combination materials herein are effective in controlling the accuracy and precision to the target site when the powder is poured or dispensed from a package (e.g., "dusting"). Further, the combination materials herein have low skin irritation and may be used on sensitive skin surfaces, such as the diapered region of a baby.

In some instances, the combination of a cellulose powder and a second (or optionally, third) powdered material may improve moisture absorption and/or oil absorption when used. Certain cellulosic materials, such as cotton as described above, have lipophilic and hydrophilic properties, and therefore absorption of one or both of water and oil may be improved through the present invention.

The present invention includes a package or kit including the first powdered material including or consisting essentially of cellulose materials and a second powdered material including or consisting essentially of starch, such as cornstarch. The package or kit includes indicia indicating the source of the materials and the amounts thereof. The package may further include a third powdered material including or consisting essentially of talc. The package may include a partially open or slotted cap to allow for pouring or dispensing of the combination powdered material to a target site.

EXAMPLES

The following examples are not intended to be limiting, but rather exemplify various embodiments of the present invention.

Example 1

Airborne Dusting Drop Test

Using the drop test as pictured in FIGS. 1A-1C, the amount of airborne particles that are released into the air after dropping a powder composition was measured. The intent was to determine the amount of particles that are released into the air after dropping various powder compositions, as well as to determine the settling time and amount after dropping is complete. It is believed that less dusting and faster settling time will allow for more controlled application of a powdered material to a target site, such as skin of a user. Various compositions including cellulose powder, cornstarch powder, talc powder, and combinations were tested.

Figure 1A:
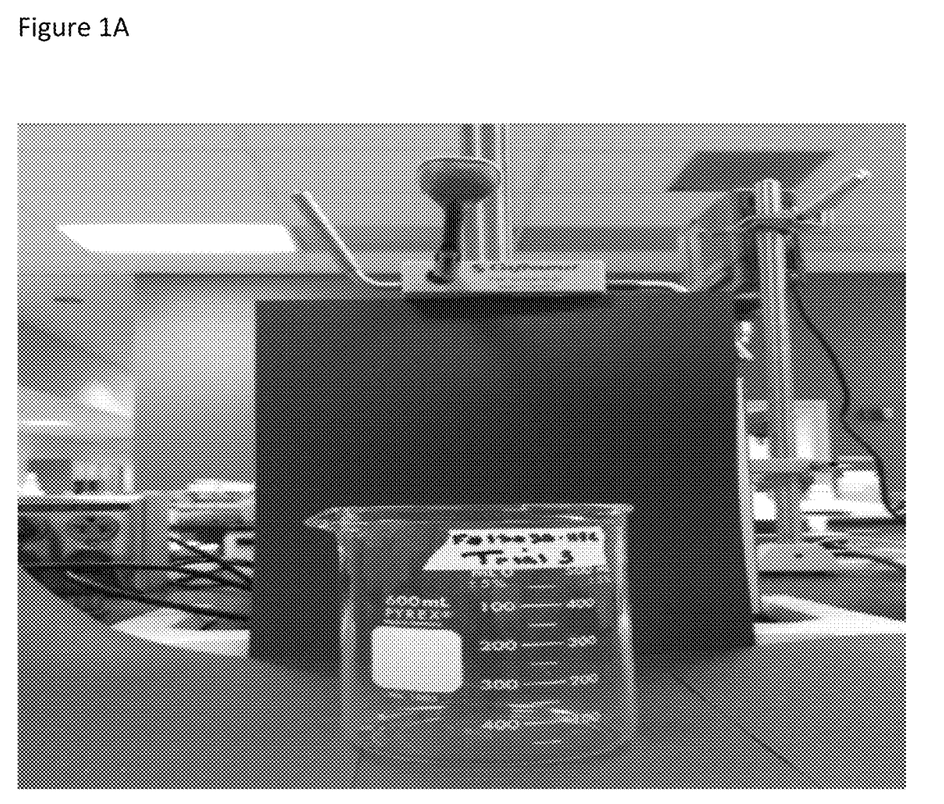
FIG. 1A shows a side view of the drop test setup.
Figure 1B:
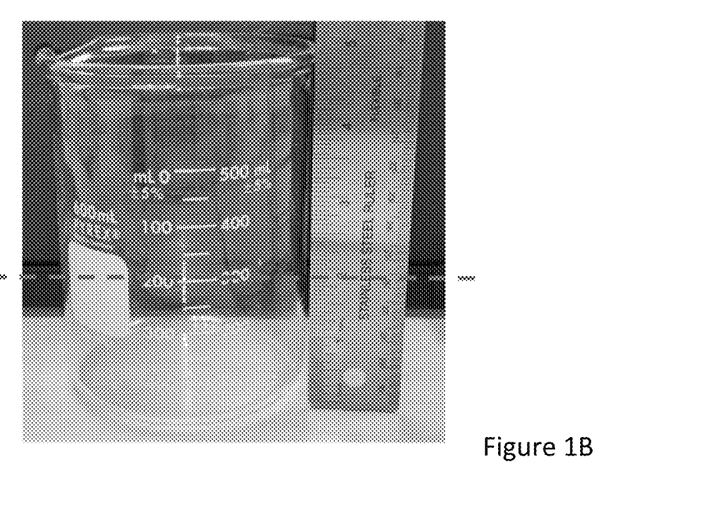
FIG. 1B shows a measurement of the beaker used in the drop test.
Figure 1C:
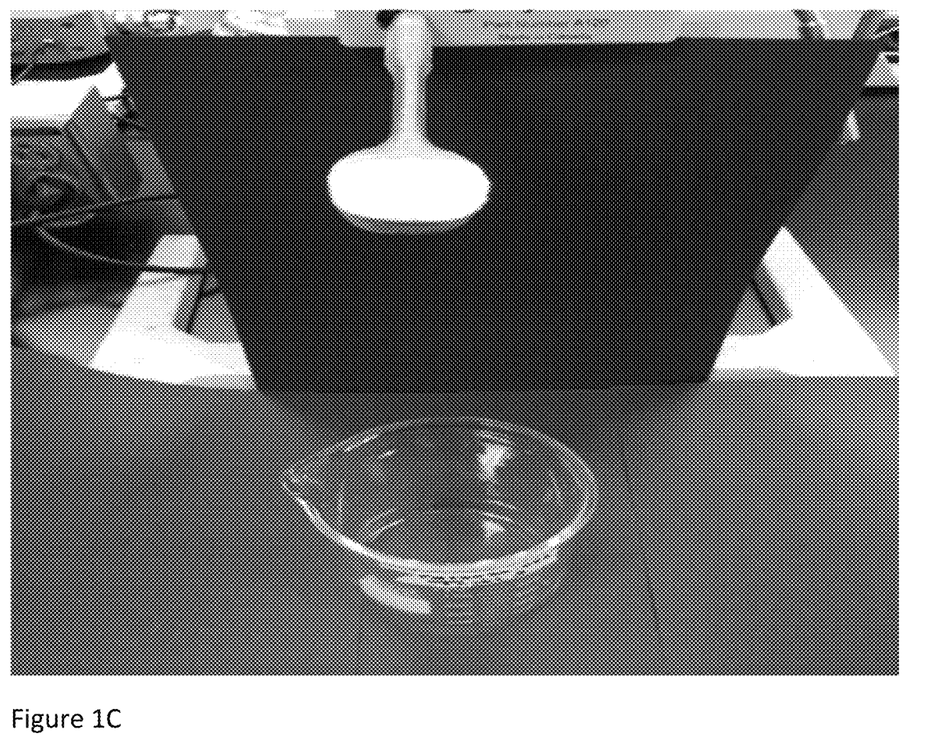
FIG. 1C shows a top view of the drop test setup.

For this experiment, a stand was used to hold a rod with a measuring spoon (one teaspoon) in a fixed location directly over an open and clean beaker. See FIGS. 1A, 1B, and 1C. The height of the spoon measured 12.5 inches from the surface and remained constant for the duration of the experiment. Amounts of each sample were measured equal by volume (though the weight of each sample was recorded for informational purposes). To prepare the sample, the rod was removed, filled to the top, and leveled off with a straight edge tongue depressor to ensure equal volume. Once filled, the rod was placed into the clamp to ensure it was held at a fixed distance from the surface. A Dylos Air Quality Monitor DC1100 PRO was placed directly in front of the beaker.

The air quality monitor was turned on and placed in continuous mode. A baseline particle count was taken for each sample before its drop into the beaker. The baseline gives the particles that are present in the surrounding environment before the sample is introduced. This was taken to ensure the surrounding air was consistent for each sample (baseline measurements were not included in the data analysis). After recording the baseline, the rod was manually turned to the right side to allow the sample to drop straight down into the beaker with minimal applied force. For these purposes, the amount of force needed to manually turn the rod to the right can be considered approximately equal for each sample tested. The major force acting on each sample is that of gravity. The intention was to provide a simple drop test that was as close to freefall as possible. Of course, it is understood that some minimal force would have to be applied to turn the sample.

As soon as the rod was turned and the product was dropped, a timer was started. Particle measurements were taken every 15 seconds for two minutes. After two minutes were complete, the monitor was turned off, removed from the area, and sprayed twice with a compressed air can, so as to clean out any particles that may have settled into any of the openings in the back. After two minutes was complete, a picture was then taken of the beaker to help visually note differences in the amount of dust produced by each sample. This shows not only the amount of dusting on the sides of beaker, but the height of the dusting that was reached due to the impact the sample had after being dropped. This experiment was repeated three times for each sample.

Figure 2:
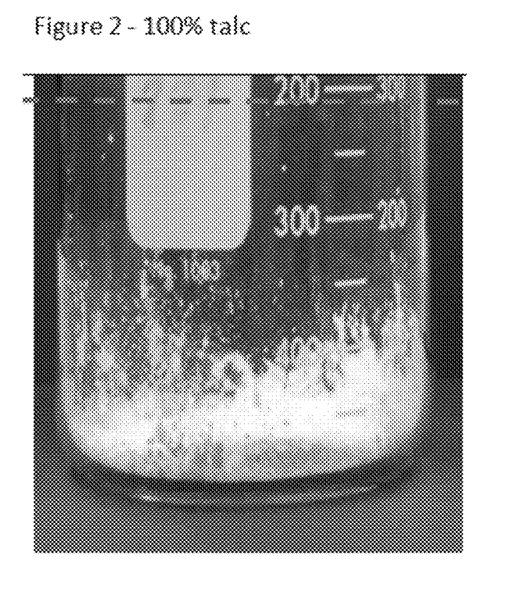
FIG. 2 shows the beaker including 100% talc after the drop test of Example 1.
Figure 3:
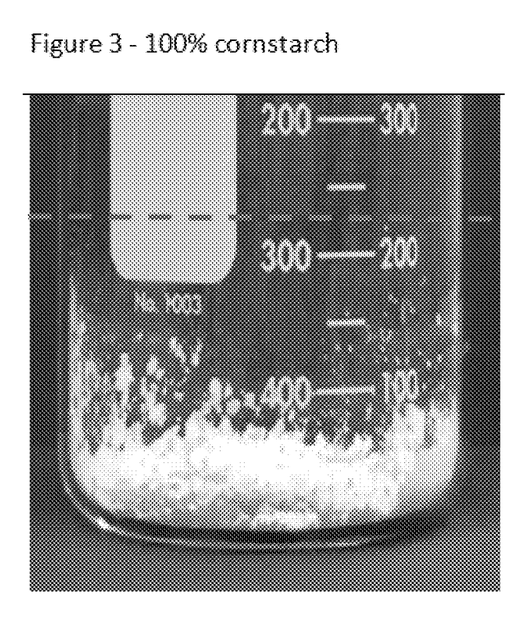
FIG. 3 shows the beaker including 100% cornstarch after the drop test of Example 1.

Five powdered samples were tested. Sample 1 was 100% cornstarch powder (Ingredion Corn Starch 034500), the corn starch having a particle size maximum of 250 microns (where 100% passed through a 60 mesh filter). Sample 2 was 100% Grade 25 USP talc powder supplied by Luzenac (where about 98.5% passed through a 74 micron (200 mesh) filter, and about 99.7% passed through a 149 micron (100 mesh) filter, and 100% passed through a 250 micron (60 mesh) filter). Sample 3 was 100% cellulose powder W325J (white cotton flock), having an average particle size of 44.04 microns in diameter and 80.20 microns in length. Sample 4 was a 50/50 blend of cornstarch powder and cellulose powder W325J. Sample 5 was a 50/50 blend of talc powder and cellulose powder W325J. A representative picture taken for 100% talc after the drop test is shown as FIG. 2; a representative picture taken for 100% cornstarch after the drop test is shown as FIG. 3; a representative picture taken for 100% cellulose particles after the drop test is shown as FIG. 4; a representative picture taken for 50%/50% cellulose particle/cornstarch after the drop test is shown as FIG. 5.

The experiment was performed three times for each sample. For each drop test run, fresh material was weighed and a new beaker was used. The Air Quality Monitor was used to measure the count of both smaller particles (>0.5 $\mu/ft^3$) and larger particles (>2.5 $\mu/ft^3$. The values both shown on the monitor and recorded during the experiment are representative of particles that are present in 0.01 $ft^3$ of sampled air. For example, the data obtained for the baseline measurement during Trial 1 of 100% Corn Starch can be described as follows: The small particle count of 272 signifies that there are 272 particles equal to or greater than 0.5 micrometers per 0.01 cubic feet of air, or 272,000 particles per cubic foot. The particle count of 3 signifies that there are 3 particles greater than or equal to 2.5 micrometers per 0.01 cubic feet of air, or 3,000 particles per cubic foot.

When turned on, the monitor automatically goes into continuous mode, which continually takes measurements until turned off. This mode was used for these experiments.

The table below shows the small particle count measurements averaged for each 15 second time point, with each of the three trials averaged below. Each total average represents an average number of particles per 0.01 cubic feet for all three trials. The baseline measurement (T=0) is not included in the Total Average.

TABLE 1

| | small particle count measurements | | | | |
|---|---|---|---|---|---|
| Time (sec) | 100% Cornstarch | 100% Talc | 100% Cellulose Powder | 50/50 Cornstarch/ Cellulose | 50/50 Talc/ Cellulose |
| 0 | 255 | 300 | 300 | 236 | 299 |
| 15 | 2747 | 12048 | 488 | 1210 | 15602 |
| 30 | 2842 | 12432 | 556 | 1572 | 19130 |
| 45 | 2731 | 12525 | 591 | 1614 | 21593 |
| 60 | 2156 | 12856 | 584 | 1691 | 21114 |
| 75 | 739 | 4411 | 358 | 944 | 11277 |
| 90 | 345 | 2096 | 277 | 436 | 4852 |
| 105 | 256 | 1096 | 238 | 308 | 1492 |
| 120 | 236 | 472 | 238 | 229 | 746 |
| Total Average | 1507 | 7242 | 416 | 1001 | 11976 |

Figure 6:
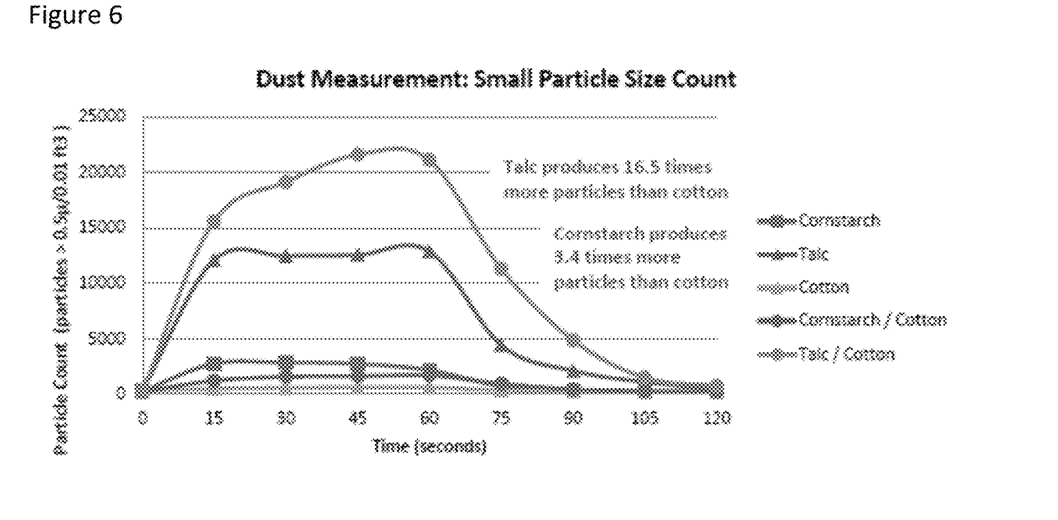
FIG. 6 shows the dust measurement for small particle sizes in Example 1.
Figure 7:
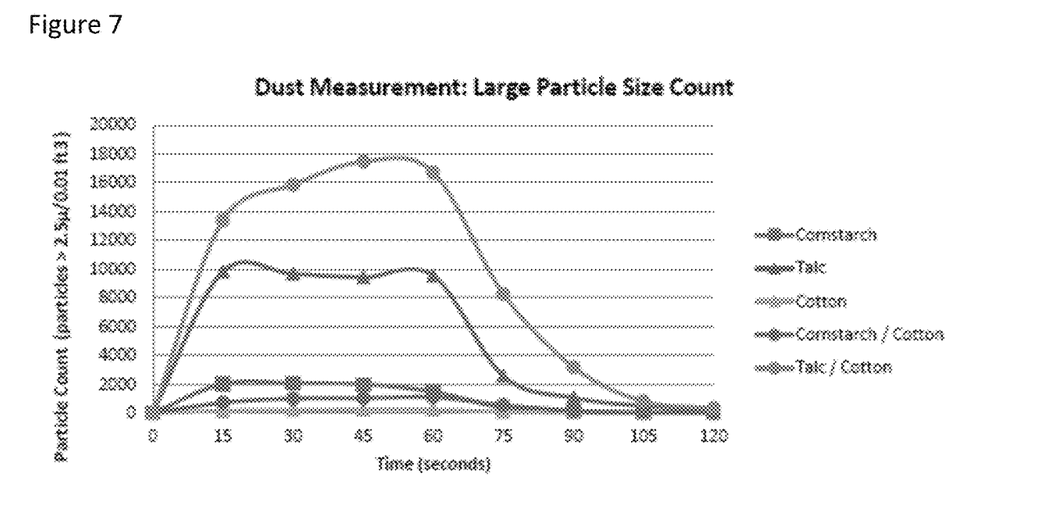
FIG. 7 shows the dust measurement for large particle sizes in Example 1.

Trends in the form of line graphs for the measurements can be seen as FIG. 6 (small particle size count) and FIG. 7 (large particle size count). These results indicate that the measurements for large and small particle sizes were consistent among the various samples.

Cornstarch produces about 3.4 times more dusting than cellulose particles itself, and cornstarch also produces about 1.4 times more dust particles than a blend of 50/50 cornstarch and cellulose particles. Talc by itself produces about 16.5 times more dusting than cellulose particles alone, and talc produces about 4.9 times as much dusting particles than cornstarch alone. Further, talc alone produces about 6.9 times as much dusting particles as the 50/50 blend of cornstarch and cellulose particles.

It was surprising that the 50/50 blend of talc and cellulose particles produced a higher degree of dusting particles than talc powder by itself. When looking at the dusting provided by individual components, it can be seen that cellulose powder by itself has the least amount of dusting, followed by cornstarch. When cellulose particles and cornstarch are combined, the result was an improved dusting profile of the blend. However, when talc and cellulose particles were combined into a blend, there was a different effect—the inclusion of cellulose particles into talc powder actually provided a greater dusting particle profile. Therefore, it cannot merely be said that the inclusion of cellulose particles into a composition will necessarily reduce its dusting profile. Rather, it is the combination of cellulose particles and cornstarch that produces a beneficial reduction in dusting particles.

Figure 4:
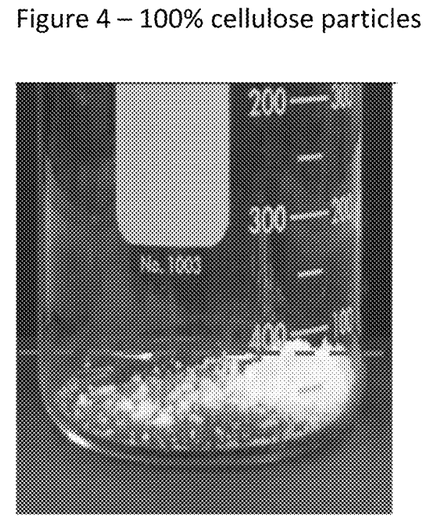
FIG. 4 shows the beaker including 100% cellulose particles after the drop test of Example 1.
Figure 5:
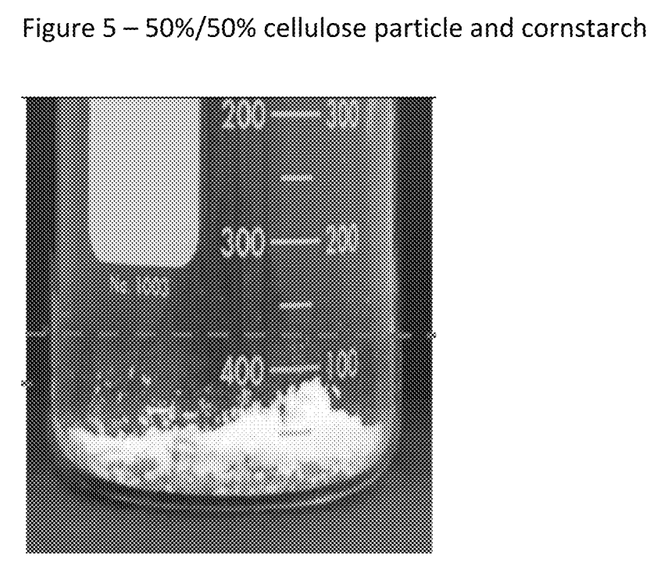
FIG. 5 shows the beaker including 50%/50% cellulose particle/cornstarch after the drop test of Example 1.

Similarly, the height of the particles adhered to the sides of the beakers was also measured to give a sense of the size of the dusting plume that is generated when dropped. Cellulose particle powder dropped by itself reached a height of 0.25 inches in the beaker (FIG. 4). Cornstarch by itself demonstrated a dusting height of 1.25 inches in the beaker (FIG. 3), while cornstarch plus cellulose particles demonstrated a height of 0.60 inches. Thus, the combination of cellulose particles and cornstarch was effective in reducing the height of the dusting plume.

Again, however, it was also surprisingly found that the combination of cellulose particles and talc again resulted in a greater dusting plume than talc by itself. Talc by itself reached a height of 2.0 inches, while the talc/cellulose combination actually exhibited a dusting plume that was higher than the size of the beaker. Conventional thinking would have been that the high dusting of talc would have been reduced by adding cellulose particles, however, the combination result exhibited greater dusting than talc by itself. This was again a result that indicates the inclusion of cellulose particles by itself into any powdered material does not necessarily reduce its dusting profile.

Example 2

Dusting With Smaller Levels of Cellulose

Compositions including smaller levels of cellulose material were tested, using the same method described above in Example 1, with the same cellulose powder W325J (white cotton flock), and similar talc and cornstarch materials. Tests were run using compositions that were hand mixed in a beaker using a tongue depressor, with ratios of: 10% cellulose and 90% cornstarch, 20% cellulose and 80% cornstarch, 10% cellulose and 90% talc, 20% cellulose and 80% talc, and 5% cellulose and 95% cornstarch. Table 2 below shows the small particle count measurements averaged for each 15 second time point, with each of the three trials averaged below. Table 3 shows large particle count measurements. Each total average represents an average number of particles per 0.01 cubic feet for all three trials. The baseline measurement (T=0) is not included in the Total Average.

TABLE 2 small particle count measurements

| Time (sec) | 10% Cellulose-90% Cornstarch | 20% Cellulose-80% Cornstarch | 10% Cellulose-90% Talc | 20% Cellulose-80% Talc | 5% Cellulose and 95% Talc |
|---|---|---|---|---|---|
| 0 | 821 | 692 | 879.3333 | 434.6667 | 1323 |
| 15 | 1219.333 | 1246.333 | 3459.333 | 1369 | 1440.666667 |
| 30 | 1429.333 | 1348.667 | 4096.333 | 1513.333 | 1449.333333 |
| 45 | 1438 | 1355 | 4167 | 1514.667 | 1483.666667 |
| 60 | 1442.333 | 1163.667 | 3450.333 | 1327.333 | 1461 |
| 75 | 942 | 737.3333 | 1279.333 | 468.3333 | 1378.333333 |
| 90 | 813 | 695.3333 | 904.3333 | 429 | 1368.333333 |
| 105 | 789 | 669.6667 | 814 | 422.3333 | 1355.666667 |
| 120 | 780.6667 | 669.3333 | 800.3333 | 416.6667 | 1327.333333 |
| Total Average | 1106.70821 | 985.6667 | 2371.375 | 932.5833 | 1408.042 |

TABLE 3 larger particle count measurements

| Time (sec) | 10% Cellulose-90% Cornstarch | 10% Cellulose-90% Talc | 20% Cellulose-80% Cornstarch | 20% Cellulose-80% Talc | 5% Cellulose and 95% Talc |
|---|---|---|---|---|---|
| 0 | 92.66667 | 89.66667 | 68.33333 | 41 | 133.3333333 |
| 15 | 440.6667 | 2492 | 483.3333 | 736 | 228 |
| 30 | 578.3333 | 2996.333 | 573.3333 | 829.3333 | 243.3333333 |
| 45 | 593.6667 | 3015.333 | 576 | 834.3333 | 271 |
| 60 | 582.3333 | 925.3333 | 426.3333 | 699 | 245.6666667 |
| 75 | 198.6667 | 344.3333 | 106.6667 | 75.33333 | 176.3333333 |
| 90 | 104.3333 | 158.6667 | 68.66667 | 53.33333 | 158.6666667 |
| 105 | 93 | 102 | 62 | 45 | 140 |
| 120 | 85.66667 | 98.33333 | 62.33333 | 43.33333 | 129.3333333 |
| Total Average | 334.583 | 1266.542 | 294.83 | 414.458 | 199.041 |

Since the baseline for airborne particles was different for different ratios tested above, the percentage increase/decrease in particles was measured. This percentage change reflects a more understandable and accurate comparison between the various ratios tested. The results are set forth in Tables 4 and 5 below.

TABLE 4

Percentage Increase-small particle count measurements

| % increase in small particle dusting | 10% Cellulose-90% Cornstarch | 20% Cellulose-80% Cornstarch | 10% Cellulose-90% Talc | 20% Cellulose-80% Talc | 5% Cellulose and 95% Talc |
|---|---|---|---|---|---|
| 0-15 | 48.52 | 80.11 | 293.40 | 214.95 | 8.89 |
| 15-30 | 74.10 | 94.89 | 365.85 | 248.16 | 9.55 |
| 30-45 | 75.15 | 95.81 | 373.88 | 248.47 | 12.14 |
| 45-60 | 75.68 | 68.16 | 292.38 | 205.37 | 10.43 |
| 60-75 | 14.74 | 6.55 | 45.49 | 7.75 | 4.18 |
| 75-90 | 0.97 | 0.48 | 2.84 | 1.30 | 3.43 |
| 90-105 | 3.90 | 3.23 | 7.43 | 2.84 | 2.47 |
| 105-120 | 4.91 | 3.28 | 8.98 | 4.14 | 0.33 |
| Avg | 37.25 | 44.06 | 173.78 | 116.62 | 7.30 |

TABLE 5 larger particle count measurements

| % increase in larger particle dusting | 10% Cellulose-90% Cornstarch | 10% Cellulose-90% Talc | 20% Cellulose-80% Cornstarch | 20% Cellulose-80% Talc | 5% Cellulose and 95% Talc |
|---|---|---|---|---|---|
| 0-15 | 375.54 | 2679.18 | 607.32 | 1695.12 | 71 |
| 15-30 | 524.10 | 3241.64 | 739.02 | 1922.76 | 82.5 |
| 30-45 | 540.65 | 3262.83 | 742.93 | 1934.96 | 103.25 |
| 45-60 | 528.42 | 931.97 | 523.90 | 1604.88 | 84.25 |
| 60-75 | 114.39 | 284.01 | 56.098 | 83.74 | 32.25 |
| 75-90 | 12.59 | 76.95 | 0.49 | 30.08 | 19 |
| 90-105 | 0.36 | 13.75 | 9.27 | 9.76 | 5 |
| 105-120 | 7.55 | 9.67 | 8.78 | 5.69 | -3 |
| Avg | 262.95 | 1312.5 | 335.98 | 910.87 | 56.75 |

Due to the measured baseline varying at different data points for various ratios of compositions, the data was normalized using percent increase in air borne particle count. For smaller particles, it can be observed that 10% cotton with cornstarch provided approximately 4.5 times less dusting than 10% cotton with talc. At the same time, the composition including 20% cotton with cornstarch provided approximately 2.5 times less dusting than 20% cotton with talc.

It was observed that as the percentage of cellulose in a talc-containing composition is increased, the dusting decreases, however, it was surprising to understand that as percentage of cotton in a cornstarch composition decreases, the resulting dusting property also decreases. As can be seen, while a composition including 10%-20% cellulose (with cornstarch) is helpful in reducing dusting, as the amount of cellulose is added to a cornstarch-containing composition, the dusting is reduced even further. This was an unexpected result, and demonstrates that the mere addition of cellulose does not provide a linear dusting reduction. It cannot therefore be said that simply adding a cellulose component reduces dusting in the same way in every composition.

Based upon the various tests conducted by the inventors, the inclusion of cellulose in a cornstarch containing composition provides a benefit in the reduction of dusting and therefore more targeted application of the composition, but the benefit of adding cellulose is not necessarily the same when used in a different composition, such as a talc-containing composition. Further, although one can see that adding a greater amount of cellulose (from 10 to 20%) in a talc composition reduces dusting, the opposite holds true for a cornstarch-containing composition, where the reduction in cellulose from 20 to 10 and to 5% actually reduced dusting greater. Further, it was noted that the 5%/95% cellulose/cornstarch composition provided a nice feel to the skin when applied, with minimal clumping or aggregation of components on the skin.

A composition including cellulose in an amount of 5%, 10% and 20% in a cornstarch-containing composition provides a benefit that was surprising to the present inventors. This result, in combination with the results seen in Example 1, demonstrates an unexpected effect when varying amounts of cellulose are added to cornstarch-containing compositions.

What is claimed is:

1. A solid powder composition to be applied to the skin comprising:
    a. a first powder component comprising corn starch powder; and
    b. a second powder component comprising a plurality of particles comprising linear hydrophobic cellulose particles, wherein said linear hydrophobic cellulose particles are derived from cotton, wherein said cotton is regenerated cotton, wherein said linear hydrophobic cellulose particles have a length of about 2 microns to about 500 microns; wherein said linear hydrophobic cellulose particles have a diameter of about 1 to about 25 microns; and wherein said linear hydrophobic cellulose particles have an aspect ratio of about 2 to about 10;
    wherein said first powder component and said second powder component are present in said solid powder composition in a ratio of about 90:10 by weight of each component; and
    wherein when said solid powder composition is applied to the skin, said cellulose particles result in reduced release of particulates into the air in the vicinity of the skin as compared to a composition comprising corn starch alone;
    wherein said solid powder composition can be more accurately applied to a target site as compared to a composition comprising corn starch alone.

2. The solid powder composition of claim 1, further comprising a third powder component comprising a plurality of particles comprising talc.

3. A method of reducing dusting of a particulate composition comprising combining a first powder component comprising corn starch powder with a second powder component comprising a plurality of particles comprising linear hydrophobic cellulose particles,
    wherein said linear hydrophobic cellulose particles are derived from cotton, wherein said cotton is regenerated cotton;
    wherein said linear hydrophobic cellulose particles have a length of about 2 microns to about 500 microns;
    wherein said linear hydrophobic cellulose particles have a diameter of about 1 to about 25 microns; and
    wherein said linear hydrophobic cellulose particles have an aspect ratio of about 2 to about 10;
wherein said first powder component and said second powder component are combined in a ratio of about 90:10 by weight of each component;
thereby forming a combination particulate composition with a lesser dusting profile than a composition that contains said first powder component without said second powder component.

4. A method of reducing skin irritation comprising the step of applying to a target skin site the solid powder composition of claim 1.

* * * * *